(12) United States Patent
Voss et al.

(10) Patent No.: US 10,238,282 B2
(45) Date of Patent: Mar. 26, 2019

(54) METHOD AND DEVICE FOR DOSAGE AND ADMINISTRATION FEEDBACK

(71) Applicant: Johnson & Johnson Vision Care, Inc., Jacksovnille, FL (US)

(72) Inventors: Leslie A. Voss, Jacksonville, FL (US); Catie A. Morley, St. Johns, FL (US); Gary S. Hall, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 761 days.

(21) Appl. No.: 13/632,862

(22) Filed: Oct. 1, 2012

(65) Prior Publication Data

US 2013/0085459 A1    Apr. 4, 2013

Related U.S. Application Data

(60) Provisional application No. 61/541,365, filed on Sep. 30, 2011.

(51) Int. Cl.
*A61M 35/00* (2006.01)
*A61B 3/113* (2006.01)
*A61F 9/00* (2006.01)
*A61B 3/10* (2006.01)

(52) U.S. Cl.
CPC ............. *A61B 3/113* (2013.01); *A61B 3/10* (2013.01); *A61F 9/0008* (2013.01)

(58) Field of Classification Search
CPC .......... A61B 3/10; A61B 3/113; A61F 9/0008
USPC .................................... 604/290, 294
See application file for complete search history.

(56) References Cited

U.S. PATENT DOCUMENTS

| | | | |
|---|---|---|---|
| 4,817,620 A * | 4/1989 | Katsuragi et al. ............. 600/401 |
| 5,042,940 A * | 8/1991 | Iwamoto .................. A61B 3/10 |
| | | | 351/208 |
| 6,039,056 A * | 3/2000 | Verbeek ..................... 134/22.18 |
| 6,749,302 B2 * | 6/2004 | Percival et al. ............... 351/208 |
| 2004/0204674 A1 * | 10/2004 | Anderson et al. .............. 604/66 |
| 2005/0001981 A1 | 1/2005 | Anderson et al. |
| 2010/0076388 A1 * | 3/2010 | Cater ..................... G01S 17/88 |
| | | | 604/298 |
| 2010/0145529 A1 * | 6/2010 | Thomason et al. .......... 700/283 |
| 2011/0122365 A1 | 5/2011 | Kraus et al. |

FOREIGN PATENT DOCUMENTS

| | | |
|---|---|---|
| EP | 2140851 A1 | 1/2010 |
| WO | WO 0158514 A1 | 8/2001 |
| WO | WO 2004028421 A1 | 4/2004 |

* cited by examiner

*Primary Examiner* — Andrew J Mensh

(57) ABSTRACT

This invention provides for a method and an EMDU used to dispense precise quantities of liquids with an image sensor being capable of providing feedback to the user as to both, when an eye is properly aligned with the EMDU, and to detect and track the quantity of the dose administered on to the eye.

25 Claims, 5 Drawing Sheets

METHOD AND DEVICE FOR DOSAGE AND ADMINISTRATION FEEDBACK

CROSS REFERENCE TO RELATED APPLICATIONS

The present application claims priority to Provisional Patent Application Ser. No. 61/541,365 filed, Sep. 30, 2011 and entitled, "METHOD AND DEVICE FOR DOSAGE AND ADMINISTRATION FEEDBACK" the contents of which are relied upon and incorporated by reference.

FIELD OF USE

This invention describes a device for dispensing precise quantities of a liquid in a discrete drop, mist or vapor, more specifically, the device having feedback capabilities used for eye alignment and administration dosage.

BACKGROUND OF THE INVENTION

It has been known to dispense a liquid or a mist into an eye using many different devices. However, although many devices result with a liquid entering the eye, the experience of getting the liquid into the eye and the dosage precision administered by the user of the devices is generally less than satisfactory.

Devices for self-dispensing liquids into the eye typically require that a user hold the eyelids open to fight the blink reflex. This contention not only inhibits easy application of the desired fluids, but also results in inconsistent dosage to the eye. Some automated devices pull down on one lid, or encapsulate the eye area to stop the lids from closing. This touch is damaging to makeup, and may lead to contamination of the device and the liquid entering the eye.

The dose from the system should consistently, without great user effort, dispense into the user's eye, not upon the eyelid or other part of the users face, and optimally should not touch the face in a manner that damages makeup or contaminates the device. Some dispensing devices simulate a 'gun' and shoot a fluid in at the eye at a rate calculated to beat the blink reflex, however the speed and impact of the fluid often induce discomfort to the patient.

Other devices force the lids open in different manners through touching the cheek below the lid, and the eyebrow range above the upper lid, then spray the fluid into the eye. This forcing open of the lids is uncomfortable, and the unit itself becomes large and unwieldy. Any makeup worn by the consumer is smudged during the process and sometimes contaminates the dispenser and/or the dispensed liquid.

Misting of fluid over the entire eye or even the facial area is also feasible, but doing so wets not only the eye, but also undesirable surfaces such as the eyelid, forehead, and nose resulting in uncertainty regarding the actual dose administered. Application of liquid to the eyelid is declared to also wet the eye by flowing into the eye, but results from this method are mixed, and the wetting of the lid itself is typically undesirable and unpredictable.

SUMMARY OF THE INVENTION

Accordingly, the present invention includes an eye medicament dispensing unit (sometimes referred to herein as "EMDU") for dispensing one or more precise quantities of medicaments or other liquids onto a surface of an eye via one or more of: a discrete drop, a mist; and a vapor. More specifically, the present invention discloses a device having an image sensor in logical connection to a microprocessor, wherein the image sensor provides an indication to the processor of one or both of: at a critical time after a blink and when an eye is properly aligned with the EMDU; and a detected quantity of a dose of a medicament administered on to the eye via the EMDU.

DETAILED DESCRIPTION OF THE INVENTION

Figure 1:
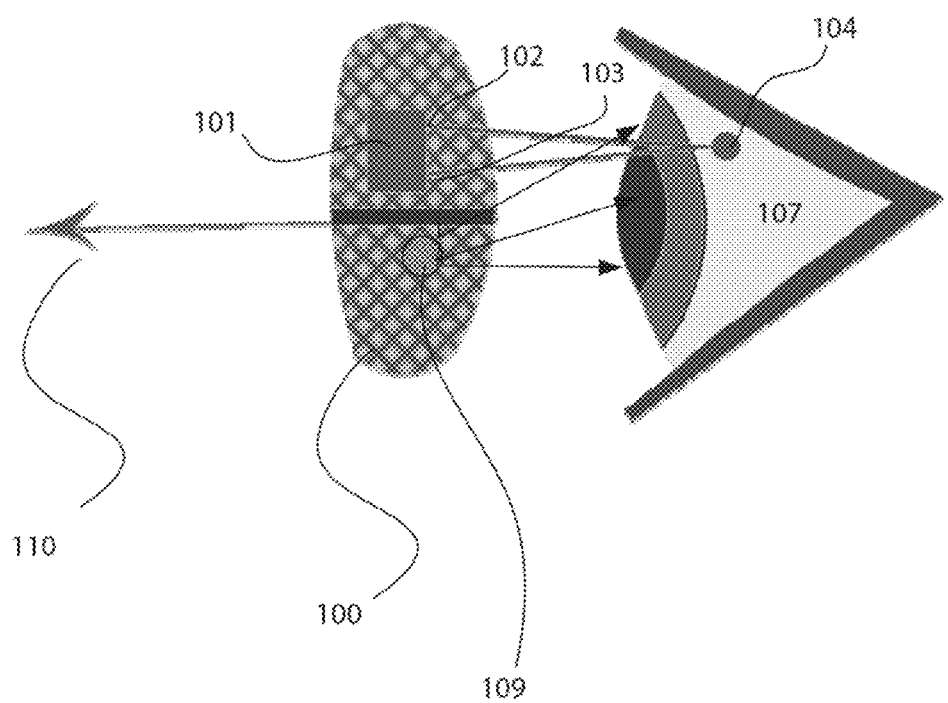
FIG. 1 illustrates an eye with an exemplary alignment apparatus within the device that may be used to implement some embodiments of the present invention.

The present invention provides for an eye liquid dispensing EMDU used to provide precise dosage administration and feedback. In the following sections detailed descriptions of embodiments of the invention will be given. The description of both preferred and alternative embodiments though thorough are exemplary embodiments only, and it is understood that to those skilled in the art that variations, modifications, and alterations may be apparent. It is therefore to be understood that the exemplary embodiments do not limit the broadness of the aspects of the underlying invention as defined by the claims.

Glossary

In this description and claims directed to the presented invention, various terms may be used for which the following definitions will apply:

"Audio Feedback" as used herein, refers to one or more corresponding audio tone(s) or series of audio tones used to provide feedback to a user. For example, Audio Feedback may be used for Alignment of the EMDU with the eye by providing a tone or beeps which may either increase or decrease significantly in pitch as the alignment of X/Y/Z axis's of the Dispensing Tip with an eye is optimized, as it may be pre-determined, for dose administration.

"Delivery Confirmation" as used herein and sometimes referred as "Dose Administration Feedback", refers to the detection of a pre-determined dose reaching the Ophthalmic Environment of a user, as intended in quantity and position. For example, measuring and sending a signal to the user in relation to the amount of medicine and the site it was dispensed onto subsequent to the administration.

"Dispensing Tip" as used herein, refers to a nozzle, valve, pump, or similar EMDU, which dispenses liquid from a liquid path to an exterior environment. "Eye Alignment" as used herein and sometimes referred to as "Alignment", refers to a positioning of an X, Y and Z axis of an EMDU in relation to an eye.

"Feedback" as used herein, refers to one or more corresponding signal(s) to the user. The signal(s) which may be, for example, a means of Audio Feedback, visual feedback (e.g. use of visual imaging or an LED light), sensory signaling (e.g. mild vibration to a part of the apparatus), to aid the user in the alignment of X/Y/Z axis's of the Dispensing Tip with an eye, a blink detection, or with Dose Administration.

"Frame Rate" as used herein, refers to a frequency (rate) at which an imaging EMDU produces unique consecutive images called frames. The term applies equally well to computer graphics, video cameras, film cameras, and motion capture systems. Frame rate is most often expressed in frames per second (FPS), and is also expressed in progressive scan monitors as hertz (Hz).

"Image Sensor" as used herein, refers to an EMDU that converts an optical image into an electronic signal. For example, one may include but is not limited to a charge coupled EMDU (CCD) or a complementary metal-oxide-semiconductor (CMOS) active pixel sensor.

"Jet Dispensing" as used herein and sometimes referred to "Dispensing", refers to a non-contact administration process that utilizes a fluid jet to form and expel droplets of liquid from the Dispensing Tip.

"Machine Vision" as used herein and sometimes referred as "Embedded Machine Vision", refers to an analysis of images to extract data for controlling a process or activity.

"Marker" as used herein, refers to a substance used as an indicator of a condition or presence. For example, a marker may include a dye present in the fluid dispensed to allow detection of the liquid in the Ophthalmic Environment.

"Ophthalmic Environment" as used herein, refers to the Dispensing area that includes Dispensing onto a surface of an eye or into an area protected by an eyelid.

"Pump" as used herein, refers to an EMDU used to transfer liquid by pumping action. May be driven with motors, solenoids, and/or air pressure.

"Steerable Dispensing Tip" as used herein, refers to a variable position Dispensing Tip controlled by software/hardware that may be included in the apparatus capable of receiving data provided by its Machine Vision System to thereby provide a signal that drives the position of the Dispensing Tip. For example, it may include automatic adjustment to minimize manual alignment required on the part of the user.

The present invention includes an EMDU for dispensing a liquid in a discrete drop, mist or vapor. The EMDU for dispensing a liquid or a mist into an Ophthalmic Environment includes a detection method to determine when an eye is Aligned. In some embodiments, dispensing may be timed to an interval based upon a determination of when an eye opens and closes, such as, for example, in a consciously induced eye blink or a natural eye blink. The blink is utilized to determine whether an eye is known to be open whereby a liquid may be dispensed before the patient closes the eye. Finally, after dispensing the EMDU may also provide accessible feedback data, for example data regarding the amount of liquid dispensed, location, time, medicine, and/or date.

Some eye dispensing EMDUs may include features that require facial contact for eye alignment. The features may require additional manual adjustment and most are not portable for everyday use. Furthermore, because facial features differ in from person to person, the preciseness and administration of the liquid onto the Ophthalmic Environment may be compromised depending facial features of the user.

The present invention provides for different embodiments that may include a sensor to provide feedback to the user for proper Eye Alignment with minimal or no facial contact. For example, Audio Feedback may be used in some embodiments to aid the user when administering liquid into the eye. Once an EMDU is properly aligned with an eye, opening and closing of the eye may also be determined by the same alignment sensor or a different dedicated sensor.

A dispensing apparatus in logical communication with the sensor may be programmed to dispense a liquid by means of discrete drops, a vapor or mist into the eye according to the timing of an open cycle of a blink. In addition, by having sensors aligned throughout the dispensing process, the EMDU may further evaluate the pre-administration state and the post administration state of the Ophthalmic Area to generate feedback data regarding the administration.

Referring to FIG. 1, an eye with an exemplary alignment apparatus within the EMDU that may be used to implement some embodiments of the present invention is depicted. At 107, an open eye provides for a reflecting point 104 on an open portion 107 of the eye, as opposed to the eyelid. The open portion of the eye 107 may include, for example, reflection of off the sclera or other portion of the eye. In some embodiments, a wavelength of an emitted beam is correlated with physical characteristics of the reflecting point 104. Reflection of the emitter beam off a predetermined portion of the eye will reflect back with a first set of reflection characteristics different from reflection off another pre-determined zone with a second set of reflection characteristics. The reflection characteristics may be sensed by the detector 103 along with a proximity sensor 109. Sensors 103 and 109 may provide data to a microprocessor which may use the data to provide Alignment feedback to the user.

In some embodiments, sensors may be replaced or used in conjunction with an Image Sensor, such as, for example, a camera capable of detecting IR to minimize ambient light interference. Alignment of an eye 107 with the liquid dispensing EMDU 100 may be facilitated by a focal point of the emitter 102 being aligned with the first and second predetermined portions of the eye, such as, for example: the sclera, iris, and/or pupil of the eye. Generally a size of an iris is consistent enough from person to person for its size in the image (along with knowledge of the field of view of the camera and some geometry) to provide distance information it may be desired to use the iris. To the contrary, the pupil may vary greatly in size as a function of ambient visible light level and other factors. Alignment may be accomplished, for example, via a line of sight 110. In some embodiments, when an iris is aligned with the line of sight 110, a sensor 101 or a camera may also be properly aligned to sense an open state and a closed state of the eye for optimal dispensing.

For example, in some embodiments, an EMDU body may include a sensor 101 and dispenser such that when a patient aligns to a Dispensing Tip in the body which forms the line of sight 110 in the dispensing EMDU, a position of the liquid dispensing EMDU 100 may then create a coaxial alignment between the line of sight and the Dispensing Tip. The Alignment establishes an angular and X-Y location of the iris relative to the dispensing EMDU 100. In embodiments where a camera sensor is used or where the EMDU further includes a proximity sensor, Z location of the iris relative to the dispensing EMDU may also be Aligned for optimal dispensing using feedback, such as, for example an audible signaling EMDU in logical communication with the sensor capable of providing Audio Feedback or one or more of an audible, sensory or visual signal. When the sensor measures a distance of the EMDU from the eye the audible signaling EMDU may signal (perhaps by click, tone, sound, or vibration,) that it is within an acceptable X,Y, Z positional range from the eye for an optimal dose. It is expected that this range will be relatively wide (in the 2-5 mm range) so any of the sensors noted above as able to detect a distance from the eye to the dispensing EMDU 100 may also be used to detect a blink as some preferred embodiments may Jet Dispense a dose based upon timing that indicates that the eyelid is involved in an opening cycle. (Dispensing of a dose during an opening cycle of an eye may be accomplished such that the patient cannot physically blink to close the eye before the liquid is dispensed.) In various embodiments, a dose may be a spray, liquid stream, discrete drop, vapor or a mist.

Figure 2:
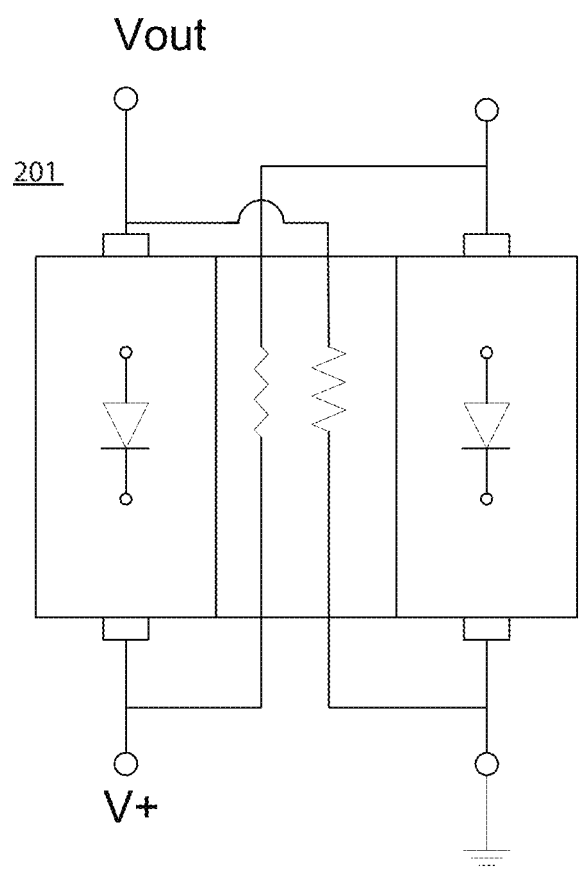
FIG. 2 illustrates an exemplary Image Sensor used for Alignment and Delivery Confirmation that may be used in The apparatus of the present invention.

Referring now to FIG. 2, an exemplary Image Sensor used for alignment and Delivery Confirmation that may be used in an EMDU of the present invention is depicted. According to the present invention, the detector 201 may be placed in logical communication with an automated dispensing unit capable of dispensing a predetermined amount of a liquid into the eye. Dispensing units are currently known and available which may receive an electrical signal based upon the logic of a sensing EMDU 101 and activates the dispensing of a dose of liquid into an eye positioned proximate to the dispensing unit. For example, an automated dispenser may include an electrically powered pump which may dispense a pulsatile liquid dose of a medicament into an eye. The electrically powered pump will respond quickly enough to allow a pulsatile dose to enter the eye before the eye may respond to the entry of the liquid into the eye. In some embodiments, the alignment/dosing feedback may be achieved using an array of sensors tied to appropriate image processing hardware and software. The combination of one or more image sensor and compatible image processing hardware and software to bring about Embedded Machine Vision. Hardware and software with image processing capabilities is already available, however, it is important that the sensors are capable of providing adequate illumination and contrast between the object being discriminated and its surroundings. An image sensor such as a camera may be used to image the eye area. A high-resolution camera may be implemented with high end, high horsepower, Machine Vision hardware, and software. The camera in some embodiments could require visible light illumination of sufficient quantity to allow the sensors to capture the object being discriminated in most surroundings. However, because some lights sources may be unpleasant to the user's eye and because CCD and CMOS image sensors (aka cameras) are inherently sensitive to both visible and near infrared light (simply called IR from here on) detection of IR light only may be advantageous in some applications. In most applications, the sensitivity to IR is undesirable as it saturates the sensor and provides no color information. For those reasons, typical cameras include a filter that blocks infrared light and passes visible light. However, to achieve illumination of the eye in a way innocuous to the user and so that it blocks ambient illumination from varying intensities, the use of IR illumination along with a camera that is only sensitive to IR light by the use of a filter may be beneficial in some embodiments. The camera is blind to the majority of the output of typical indoor lighting but may provide its own localized IR illumination. Furthermore, an additional benefit of the use of IR pass filtering and IR illumination may be that the contrast of the pupil against the iris may be better under those conditions.

The infrared emitter and detector may be placed in close proximity to the eye. The emitter and detector may be oriented such that the detector does not "see" the emitter directly but may only receives IR that is reflected off a surface in front of the emitter and detector. When the eyelid is closed, the reflectance is greater than when the eyelid is open. Thus, to the detector, a blink, and/or X,Y,Z positioning due to contrast may apparent as a rapid increase in IR input followed by a rapid decrease in IR input. The increase and decreases in reflectivity are determined by calculating a simple delta between successive detector samples.

In some embodiments of the present invention, a Marker may also be added to the liquid being dispensed. Using a Marker, e.g. a dye in the medicine, may allow for Delivery Confirmation vie Machine Vision used. Machine Vision may be further used for other things, e.g. to read barcodes, track medicine remaining, detect glare of IR light for Z alignment, etc. For example, if the medicine container for the EMDU is refillable vs. disposable, the user could be prompted to point the EMDU at a code on the box/cartridge to confirm that it is compatible. Finally, Machine Vision may also be used to combine the embedded machine vision system with a "steerable" nozzle to minimize the need for manual alignment on the part of the user.

Additionally, image processing hardware may be implemented using programmable logic EMDUs, such as CPLDs or FPGAs, microcontrollers, microprocessors, and application specific integrated circuits (ASICs). The processing hardware may be inside the EMDU or merely in connection with the EMDU i.e. a cell phone, computer, or TV in connection with the dispensing EMDU through Bluetooth.

Figure 3:
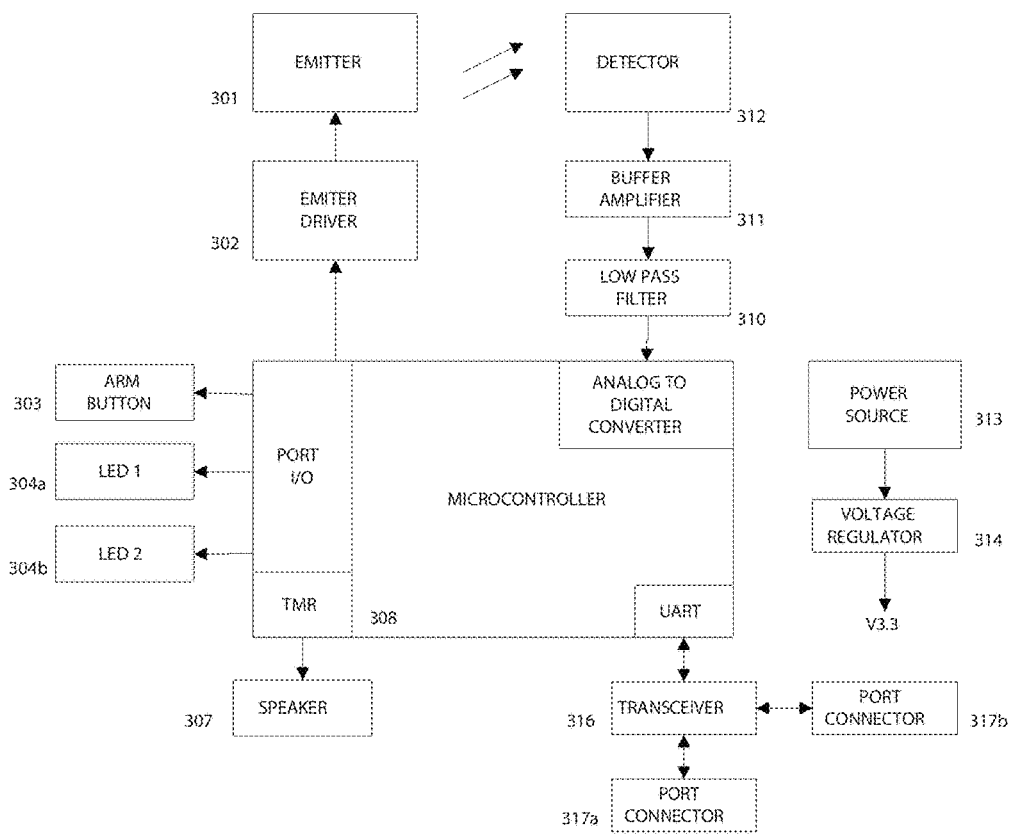
FIG. 3 illustrates a block diagram of an exemplary EMDU used to implement the present invention.

Referring now to FIG. 3 a block diagram of an exemplary hardware used to implement the present invention is depicted. At 308, a microcontroller is shown. The microcontroller depending on the embodiment should be capable of customized configuration for proof of principle design. For example, one suitable microcontroller may include, a Cypress Semiconductor CY8C29466 microcontroller.

An application specific integrated circuit (ASIC) may also be suitable in other simplified embodiments/applications. The microcontroller 308 may receive data from one or more detector(s), for example a proximity detector such as an Avago HSDL-9100 proximity detector 312 infrared emitter/detector 301 pair in a single package. When using one as the emitter/detector package, constant current driver 302 circuitry for the emitter and a means for voltage conversion 311, buffering, or filtering 310 for the photodiode output may be desired in some embodiments. Additionally in connection to the microcontroller 308 a feedback indicator (e.g. a visual indicator 304a/304b), audible indicator (e.g. speaker 307), power source 313 (and a voltage regulator 314 depending on the power source used), user interphase 303 (e.g. a button), and a transceiver 316 with one or more port connectors 317a/317b may be integrated.

Figure 4:
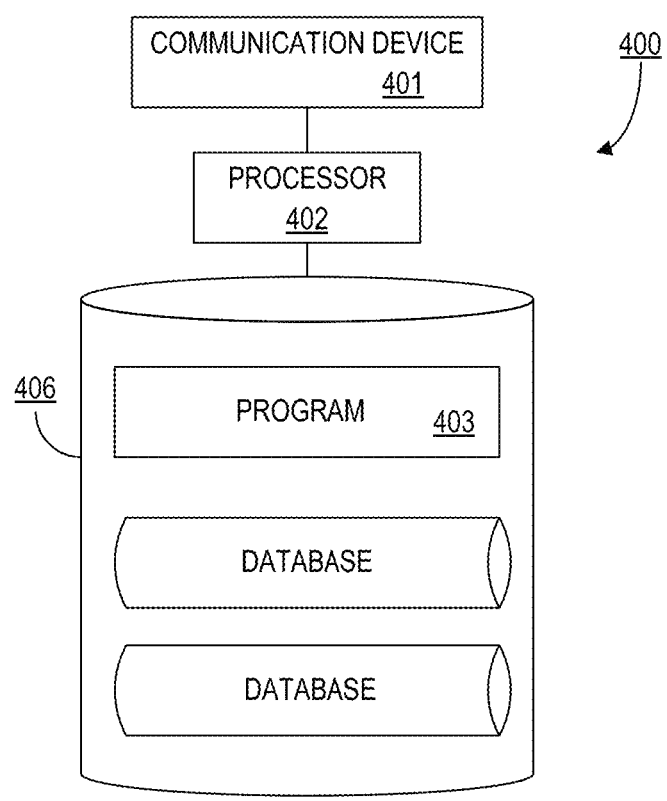
FIG. 4 illustrates a microcontroller that may be used to in some embodiments of the present invention.

Referring now to FIG. 4 a microcontroller that may be used to implement some embodiments of the present invention is depicted. At 400, an exemplary controller is illustrated. The controller 400 includes a processor 402, which may include one or more processor components coupled to a communication device 401.

In some embodiments, a controller 400 may be used to receive a logical indication of the X, Y, Z position in relation to a zone of the eye and/or that an eye is in a first state or a second state and transmit energy to liquid dispenser at a time appropriate to dispense a liquid or mist into the eye, based upon the transition from a first state to a second state. A controller 400 may include one or more processors, coupled to a communication device 401 configured to communicate energy via a communication channel. The communication device 401 may be used to electronically control, for example, one or more of Alignment; timing of liquid dispensing; an amount of liquid dispensed; duration of a dispensing motion, tracking a number of dispensing actions, tracking chronological dispensing patterns or other actions related to the dispensing.

The processor 402 is also in communication with a storage device 406. The storage device 406 may comprise any appropriate information storage EMDU, including combinations of magnetic storage EMDUs (e.g., magnetic tape and hard disk drives), optical storage EMDUs, and/or semiconductor memory EMDUs such as Random Access Memory (RAM) EMDUs and Read Only Memory (ROM) EMDUs. The storage device 406 may store a program 403 for controlling the processor 402. The processor 402 performs instructions of the program 403, and thereby operates in accordance with the present invention. For example, the processor 402 may receive information descriptive of liquid to be dispensed, dispensing amounts, dispensing patterns, and the like.

Figure 5:
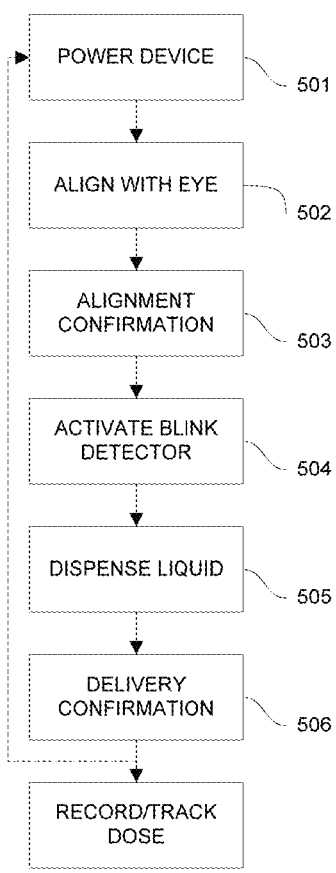
FIG. 5 is a flowchart showing a method of implementing the present invention.

Referring now to FIG. 5, a flowchart illustrates a method of implementing some embodiments of the present invention. At 501, the user of the EMDU may activate the EMDU when Dispensing is required. The EMDU may be powered through a button, switch or by motion detection depending on the embodiment. At 502, subsequent to activating an EMDU, a user may place the EMDU in proximity to a place where dispensing of liquid is desired. The EMDU may then provide feedback (e.g. visual or audible) to help align the EMDU with the eye for dispensing until Alignment confirmation 503 is sent by the EMDU. Upon receiving Alignment confirmation 503, the EMDU's blink detector may be activated 504 and thereby detect a blink. The blink acts as input to trigger dispensing of a liquid 505 subsequent to detection of the blink, and before the user may blink again.

At 506, Delivery Confirmation of the liquid is recorded by the EMDU. Using the data recorded, the EMDU may send to a compatible EMDU or use the data to determine one or more of a plurality of things/events. For example; verifying, tracking, and/or activating a future reminder of the dose.

CONCLUSION

The present invention, as described above and as further defined by the claims below, provides methods of providing a liquid dispenser with a feedback mechanism used for Dose Verification and/or Alignment.

The invention claimed is:

1. An apparatus for dispensing liquid into an ophthalmic environment, the apparatus comprising:
   an emitter configured to emit radiation of a wavelength toward an eye, the emitter having a focal point aligned with a first portion of at least one of the sclera, iris and pupil of the eye wherein the radiation reflects off the portion of the eye generating a reflecting wavelength containing a set of reflection characteristics;
   an automated dispenser for dispensing a liquid towards the eye based upon receipt of a logic signal;
   an alignment sensor configured to detect the reflecting wavelength and to determine whether the dispenser is in proper alignment with a predetermined ophthalmic region based on the characteristics of the reflecting wavelength;
   at least one blink detector configured to detect a blink of an eyelid of the eye; and
   a processor in logical communication with at least one of the emitter, the alignment sensor, the blink detector, and the automated dispenser, wherein the processor is configured to receive a signal indicating a first blink of the eyelid and, upon receipt of the signal indicating the blink, to trigger dispensation of the liquid; wherein the dispensation is programmed to occur in a period calculated to transpire before a second blink of the eyelid is physiologically possible.

2. The apparatus of claim 1, wherein the automated dispenser is functional to dispense liquid based upon receipt of a transmitted logic signal associated with the eye being in an open state.

3. The apparatus of claim 2, wherein the transmitted logic signal coordinates dispensing of liquid towards the eye.

4. The apparatus of claim 1, wherein the alignment sensor comprises a camera.

5. The apparatus of claim 4, wherein the camera comprises an infrared camera.

6. The apparatus of claim 5, wherein the infrared camera further comprises an infrared filter.

7. The apparatus of claim 1, further including a digital storage storing executable software operative with the processor to cause the processor to be functional to coordinate dispensing of the liquid towards the ophthalmic region based upon a detection of the reflecting wavelengths reflected off the eye.

8. The apparatus of claim 7, further including a dispensing nozzle in fluid communication with the automated dispenser and functional to jet dispense liquid.

9. The apparatus of claim 8, wherein the dispensing nozzle is a steerable nozzle in logical connection with an alignment sensor.

10. The apparatus of claim 9, further comprising a feedback signaling device in electrical communication with the alignment sensor, the feedback signaling device configured to be activated based upon a signal from the alignment sensor.

11. The apparatus of claim 10, wherein the feedback signaling device is an audible signaling device capable of emitting audible signals to the user for alignment.

12. The apparatus of claim 10, wherein the feedback signaling device is a visual signaling device capable of providing a visual signal to the user for alignment.

13. The apparatus of claim 10, wherein the feedback signaling device is a sensory signaling device capable of providing a change for sensory nerves of the user for alignment.

14. The apparatus of claim 10, wherein the feedback signaling device comprises a combination of audible and visual signaling.

15. The apparatus of claim 10, wherein dispensing of the liquid is based upon receipt of a signal indicating the ophthalmic region is aligned.

16. The apparatus of claim 15, wherein dispensing of the liquid is further based upon the receipt of a signal indicating the eye is in an open state.

17. An apparatus for dispensing liquid into an ophthalmic environment, the apparatus comprising:
   an automated dispenser for dispensing a liquid towards an eye based upon receipt of a logic signal;
   an emitter configured to emit radiation of a wavelength toward the eye, the emitter having a focal point aligned with a first portion of at least one of a sclera, iris and pupil of the eye, wherein the radiation reflects off of the first portion of the eye with a set of reflection characteristics;
   a camera configured to detect the radiation reflected from the eye, wherein the camera is configured to detect a blink of an eyelid of the eye and whether the automated dispenser is in proper X, Y, Z alignment with a predetermined ophthalmic region based on the characteristics of the reflecting wavelength; and a processor in logical communication with at least one of the emitter, the camera and the automated dispenser, wherein the processor is configured to receive a signal indicating a first blink of the eyelid and, upon receipt of the signal indicating the first blink, to trigger dispensation of the liquid; wherein the dispensation is programmed to occur in a period calculated to transpire before a second blink of the eyelid is physiologically possible.

18. The apparatus of claim 17, wherein the camera comprises an infrared camera.

19. The apparatus of claim 18, wherein the infrared camera further comprises an infrared filter.

20. The apparatus of claim 17, further comprising a feedback signaling device in electrical communication with the camera, wherein the feedback signaling device is capable of being activated based upon a signal from the camera.

21. The apparatus of claim 20, wherein the feedback signaling device is an audible signaling device capable of emitting audible signals to the user for alignment.

22. The apparatus of claim 20, wherein the feedback signaling device is a visual signaling device capable of providing a visual signal to the user for alignment.

23. The apparatus of claim 20, wherein the feedback signaling device is a sensory signaling device capable of providing a change for sensory nerves of the user for alignment.

24. The apparatus of claim 20, wherein the feedback signaling device comprises a combination of audible and visual signaling.

25. The apparatus of claim 9, wherein the apparatus for dispensing liquid into an ophthalmic environment is configured to be handheld.

* * * * *